(12) United States Patent
Prasad

(10) Patent No.: US 6,627,248 B1
(45) Date of Patent: Sep. 30, 2003

(54) METALLIZATION OF CERAMIC RESTORATIONS

(75) Inventor: Arun Prasad, Cheshire, CT (US)

(73) Assignee: Jeneric/Pentron Incorporated, Wallingford, CT (US)

(*) Notice: Subject to any disclaimer, the term of this patent is extended or adjusted under 35 U.S.C. 154(b) by 0 days.

(21) Appl. No.: 09/710,051

(22) Filed: Nov. 10, 2000

(51) Int. Cl.⁷ .............................................. A61C 13/09
(52) U.S. Cl. ............ 427/2.26; 427/2.29; 427/205; 433/201.1; 433/202.1
(58) Field of Search ............... 428/699, 701, 428/702, 293.1, 312.8, 304.4, 306.6, 307.3, 307.7, 312.2, 318.4, 319.1; 427/204, 205, 229, 250, 252, 192.15; 433/222.1, 228.1, 201; 264/19; 623/16; 106/35

(56) References Cited

U.S. PATENT DOCUMENTS

| | | |
|---|---|---|
| 3,502,466 A | 3/1970 | Vickery |
| 3,631,631 A | 1/1972 | Greenstein |
| 4,073,999 A * | 2/1978 | Bryan et al. ................ 427/226 |
| 4,189,838 A | 2/1980 | Olivia |
| 4,318,697 A | 3/1982 | Shoher |
| 4,369,068 A | 1/1983 | Hausselt |
| 4,650,418 A | 3/1987 | Blair |
| 4,689,197 A | 8/1987 | Groll |
| 4,781,590 A | 11/1988 | Weisnstein |
| 4,828,495 A | 5/1989 | Bell |
| 4,879,136 A | 11/1989 | Polz |
| 4,952,151 A | 8/1990 | Metcalfe |
| 4,970,032 A | 11/1990 | Rotsaert |
| 4,980,124 A | 12/1990 | Dimmer |
| 5,104,323 A | 4/1992 | Mertens |
| 5,151,044 A | 9/1992 | Rotsaert |
| 5,203,698 A | 4/1993 | Blake |
| 5,232,492 A | 8/1993 | Krulik |
| 5,346,717 A * | 9/1994 | McCrory ................ 204/192.1 |
| 5,814,682 A | 9/1998 | Rusin |
| 5,939,211 A | 8/1999 | Mormann |
| 5,951,293 A * | 9/1999 | Billet et al. ................ 433/218 |
| 6,048,205 A * | 4/2000 | Wright .................... 433/200.1 |
| 6,322,728 B1 * | 11/2001 | Brodkin et al. ............... 264/19 |
| 6,345,984 B2 | 2/2002 | Karmaker et al. |
| 6,354,836 B1 | 3/2002 | Panzera et al. |
| 6,403,212 B1 * | 6/2002 | Shoher et al. ............. 29/896.1 |

FOREIGN PATENT DOCUMENTS

| | | | |
|---|---|---|---|
| DE | 19503637 A1 | 8/1996 | |
| EP | 523 019 A1 | 1/1993 | |
| EP | 883586 * | 12/1998 | ........... C04B/28/28 |
| EP | 1 006 095 A1 | 6/2000 | |
| EP | 1006095 A2 * | 6/2000 | |
| WO | WO 92/00935 | 1/1992 | |

OTHER PUBLICATIONS

International Preliminary Examination Report for International Application No.: PCT/US00/42044. No Date.

Perkins, Walter W., Editor, Ceramic Glossary, 1984, The American Ceramic Society, pp. 13, 14, 37. No Month.

* cited by examiner

*Primary Examiner*—Deborah Jones
*Assistant Examiner*—Arden Sperty
(74) *Attorney, Agent, or Firm*—Ann M. Knab

(57) ABSTRACT

A dental restoration comprises a ceramic core material having a thin metallic layer disposed on the interior surface of the ceramic core to provide integrity to the ceramic core, eliminate bonding between the ceramic core and the patient's tooth or teeth, and provide an impervious layer on the ceramic interior to reduce infiltration of fluids into the ceramic and reduce cracking of the ceramic restoration. The metallic layer may comprise a metal, alloy or metal-matrix ceramic material. A strong, crack-resistant ceramic restoration is provided having highly aesthetic properties.

7 Claims, 1 Drawing Sheet

10

METALLIZATION OF CERAMIC RESTORATIONS

FIELD OF THE INVENTION

This invention relates to the manufacture of dental restorations and more specifically to the fabrication of ceramic dental restorations and to the metallization of the internal surfaces of the ceramic restorations.

BACKGROUND OF THE INVENTION

Fracture analyses of failed all-ceramic restorations reveal that the cracks typically initiate from their internal surfaces. These cracks may be initiated from the flaws that may develop from processing, etching or abrading of the ceramic surface that is required to improve the bonding between the ceramic and the tooth to which it is to be bonded. Use of resin-based adhesives in combination with resin based cements has been recommended to reduce such failures by providing an adequate bond between the cement and the ceramic and between the cement and the tooth. This has definitely improved the service life of the restorations. However, resin based adhesives and cements imbibe water. Therefore, the interface between resin adhesives and ceramics is not truly impervious to water. It is well known that mechanical properties of ceramics are lower in wet conditions. Also, it is to be noted that the moduli of these cements are lower than the moduli of the dentin or all-ceramic restorative materials. Therefore, crack-initiation and propagation may result from the combined effects of stress-corrosion at the interface and cyclic fatigue. Furthermore, the resin does not always fill in the crevices and surface etchings that result from the etching process and such crevices may lead to crack propagation.

To reduce or eliminate the cracking problems, porcelain-fused-to-metal (PFM) restorations have been fabricated whereby a metal core is manufactured and thereafter porcelain is fused to the metal core. The metal not only supports the porcelain veneer due to bonding and differential contraction but also offers an impervious layer for fluid penetration. Also it is conventional to use zinc phosphate or non-resin modified glass-ionomers cements for cementation of these PFM restorations. Interestingly, the moduli of such cements are higher than that of the resin-based alternatives.

It is desirous to eliminate the lost wax process and create a more efficient and simplified process for the manufacture of a dental restoration. It is beneficial to reduce the amount of metal employed in the manufacture of dental restorations to provide a more aesthetic appearance. Dental practitioners also prefer not to use resin-based adhesives/cements as they are time consuming and technique sensitive.

SUMMARY OF THE INVENTION

These and other objects and advantages are accomplished by the materials and methods of the present invention comprising a ceramic core material having a thin metallic layer disposed on the interior surface of the ceramic core to provide integrity to the ceramic core, eliminate bonding between the ceramic core and the patient's tooth or teeth, and provide an impervious layer on the ceramic interior to reduce infiltration of fluids into the ceramic and reduce cracking of the ceramic restoration. The metallic layer may comprise a metal, alloy or metal-matrix ceramic material.

In one embodiment of the method of the invention, the ceramic core structure is fabricated. Thereafter, the metallic layer is applied to the interior surface of the ceramic core by known techniques such as electrolytic or electroless deposition, sol/gel deposition followed by pyrolysis, fusing (sintering), pressing, sputtering, chemical vapor deposition, ion bombardment, and vacuum deposition.

In another embodiment of the method herein, a metal or metal-matrix ceramic material is first formed into a thin core structure. Thereafter, a ceramic material is applied to the thin layer of metal or metal-matrix ceramic material by known techniques such as electrolytic or electroless deposition, sol/gel deposition followed by pyrolysis, fusing (sintering), pressing, sputtering, chemical vapor deposition, ion bombardment, and vacuum deposition.

A strong, crack-resistant ceramic restoration is provided having highly aesthetic properties.

BRIEF DESCRIPTION OF THE DRAWINGS

Features of the present invention are disclosed in the accompanying drawing, wherein.

DESCRIPTION OF THE INVENTION

Figure 1:
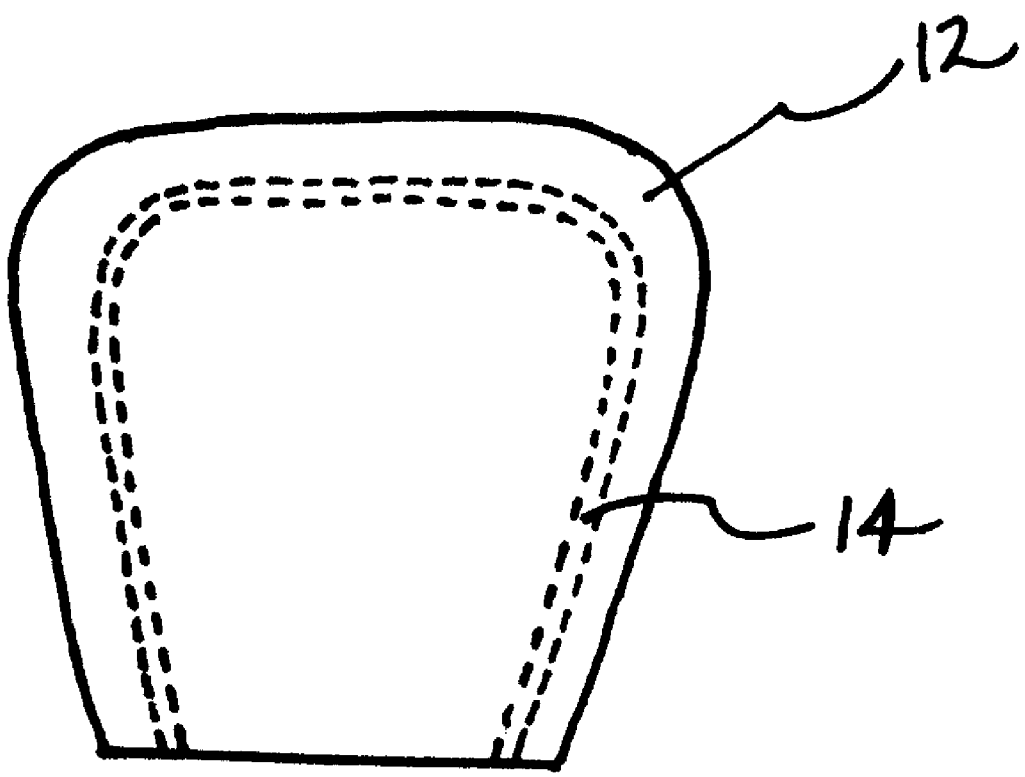
FIG. 1 is an elevational view of a dental restoration in accordance with the invention.

As will be appreciated, the present invention is directed to materials and methods for manufacturing dental restorations. In accordance with one embodiment herein, a ceramic infrastructure is fabricated to provide a strong core material. The core material is from about 0.5 to about 5 mm in thickness and provides integrity and strength to the final dental restoration. Conventional methods may be used to fabricate the core material, although it is necessary that the internal structure of the core material be larger than the tooth or teeth onto which it is to be positioned. The core material may be fabricated of any known ceramic material such as glass-ceramics or porcelains, all-ceramic materials or amorphous glass materials. Suitable ceramic materials include alumina, zirconia, mullite, silica, silicates, spinel, titania, lithium disilicate, leucite, lithium phosphate, and combinations thereof.

Preferably, the internal or understructure of the ceramic core is made larger than the tooth or teeth on which it is to be placed. One method of fabrication would involve fabricating a die larger than the actual tooth or teeth on which the ceramic restoration is to be placed. Alternatively, CAD/CAM methods and equipment can be used to fabricate the core and/or the die. With respect to the die, the die could be machined by CAD/CAM methods to be larger than the actual tooth. With respect to the core, the understructure of the core would be machined by CAD/CAM methods to be larger than the location on which it is to be positioned. If the restorations are fabricated using CAD/CAM techniques, the software can build in this extra dimension to the scanned data. The setting expansion of the die materials can also be regulated to obtain enlarged dies. U.S. Pat. Nos. 5,939,211, 5,151,044, 4,970,032, commonly assigned copending application Ser. No. 09/344,089 filed Jun. 25, 1999, now U.S. Pat. No. 6,345,984, and copending, commonly owned application Ser. No. 09/376,921 filed Aug. 18, 1999, now U.S. Pat. No. 6,354,836, are directed to materials and methods of producing dental restorations using CAD/CAM techniques and are hereby incorporated by reference.

The die is made from about 0.1 to about 5 percent and preferably from about 1 to about 2 percent larger than the actual tooth or teeth to provide for application of a layer of material under the ceramic core. After fabrication of the die, the ceramic material is applied to the die by known processes to produce the ceramic core.

Likewise, if a die is not used and the ceramic core is fabricated using CAD/CAM techniques, the understructure of the core is made larger than the tooth or teeth to which it will be applied to allow for application of an impervious layer of material on the surface of the internal side of the ceramic core. The thickness of the ceramic core is from about 0.5 to about 5 mm and preferably from about 0.6 to about 1.5 mm in thickness. The internal dimensions of the ceramic core should be from about 0.1 to about 5 percent, and preferably from about 1 to about 2 percent larger than the tooth or teeth on which it will be positioned to accommodate the impervious layer.

After the ceramic core is fabricated, a very thin layer of a metal or metal-matrix-ceramic (MMC) material is applied to the internal side or understructure of the ceramic core. This internal layer is applied to act as a barrier to any fluids that could internally permeate into the ceramic material, which although is very strong, is not completely impervious to fluids. Moreover, the formation of cracks is reduced or eliminated on the interior surface of the ceramic due to the elimination of the etching or abrading step on the ceramic surface and also due to higher resilience of the impervious layer. Due to the application of the impervious layer, the internal ceramic surface is not directly bonded to the tooth surface. It is the metal or MMC layer that actually bonds the ceramic restoration to the tooth, thereby eliminating the etching of the ceramic surface. The metal or MMC layer is not as susceptible to cracking due to abrading. Please refer to FIG. 1 which shows a restoration 10 having a ceramic core 12 and a thin metallic layer 14 disposed on the internal side of ceramic core 12.

The metal or metal-matrix-ceramic material is applied to the internal side in any known manner including, but not limited to electrolytic or electroless deposition, sol/gel deposition followed by pyrolysis, fusing (sintering), sputtering, chemical vapor deposition, ion bombardment, and vacuum deposition. If the internal layer is fused to the ceramic core, the processing temperature should be lower than the fusion temperature of the ceramic core, preferably about 100° C. below the fusion temperature range of the ceramic material to prevent distortion. The thickness of the internal layer is very thin, below about 200 microns and most preferably below about 100 microns. The internal layer is substantially impervious to fluids and prevents fluid penetration and increases resistance to stress-corrosion. It also reduces crack formation in the ceramic core due to the elimination of the etching/abrading of the ceramic surface. The coefficient of thermal expansion is not very critical due to the thinness of the layer. Examples of metals for use in the metal layer or MMC layer include, but are not limited to, gold, silver, platinum group metals, titanium, tin, indium, gallium, antimony, and mixtures thereof. The metal or MMC material may be in the form of powder (preferably with binder), or a more fluid suspension such as an organo-metallic mixture or a resinate mixture, or in the form of a film or thin tape or sheet (with or without the addition of a vehicle). It is preferred that the color of the impervious metal or MMC layer is yellow to provide aesthetic acceptable restorations. A bonding agent such as Gold Bonder™ powder available from Jeneric/Pentron Inc., Wallingford, Conn. may be applied to the internal surface of the ceramic core prior to application of the impervious layer thereto.

The impervious layer can be formed using techniques described above. The techniques may include single or multiple steps. For electrolytic deposition, a conductive varnish on the internal surfaces is to be applied to obtain electrical continuity. Silver or gold conductive varnishes are commercially available for electronic applications. U.S. Pat. No. 5,232,492 is directed to electroless plating and is incorporated herein by reference. For a sintering approach, a thin layer can be formed from a metal suspension via spraying or brushing techniques. The applied layer can be fired to remove the binder and to attain high density. Thermal treatment will also improve the bonding of the impervious layer to the glass-ceramic substrate. Such thermal treatments need be performed below the processing temperature of the glass, ceramic or glass-ceramic to prevent distortion. Examples of commercially available coatings useful herein include Liquid Bright Gold™ and Liquid Bright Platinum™ suspensions in the form of films, metal resinates (reaction product of an organic compound with a metal salt), or metallo-organics (metal compounds in organic solvents), all available from Engelhard Industries, N.J. Other commercially available materials include Galvanokor™ materials available from Jeneric/Pentron Inc., Wallingford, Conn.

In a preferred embodiment, the metal or MMC layer to be applied to the ceramic is in the form of powder. The metal powder is used in combination with a vehicle, such as a binder material, to hold the metal particles together for easier application or adaptation to the ceramic core. The combination metal powder/binder is preferably in a paste or sheet form. Accordingly, the paste may be pressed onto the internal surface or the ceramic core or the sheet may be cut to a desired shape to fit into the internal surface or the ceramic core.

Typical binder materials include, but are not limited to filler-free wax, ammonium caseinate, ammonium stearate, pectin, hexamine, ethyl cellulose, anthracene, triacetyl starch, dulcin, carbazole and tetraphenyl ethylene. The binder may be mixed with a solvent prior to mixing with the metal powder. Solvents include, without limitation, propylene glycol, water, eugenol, light paraffin oil, butyl acetate, butyl benzoate, diacetone alcohol, and dibutyl phthalate. The binder and solvent are driven off during the sintering process.

The powder/binder mixture comprises from about 90 to about 99 percent powder and from about 1 to about 10 percent binder. Preferably, the powder is present in about 96% by weight and the binder is present in about 4% by weight.

The metal powder is preferably a high fusing metal and may comprise one or more precious metals, non-precious metals and alloys thereof. Preferably, the metal powder comprises a non-oxidizing metal. More preferably, the metal powder is selected from one or more of gold, silver, platinum group metals, titanium, tin, indium, gallium, antimony, rhodium, palladium, an organometallic material, and mixtures thereof. One preferred alloy comprises about 85 to about 99% Au, 0 to about 15% Pt, and 0 to about 15% of one or more of Ga, Zn, Ge, Cu, Sn, Ti, Ag, Pd, Rh, In, Ru, and Ta. The particle size of the powder is in the range of from about 0.1 to about 150 microns and preferably from about 0.1 to about 40 microns. The powder may come in a variety of forms, including, but not limited to, flakes, spheres, spheroids, or any other known shape.

The metal powder may comprise a multimodal particle size distribution to achieve high density during sintering. The multimodal particle powder comprises larger or coarse particle size powder in combination with a smaller or fine particle size powder. The maximum size of the coarse particle powder is preferably equal to or less than about —100 mesh. The particle size range is preferably from about 1 to about 150 microns and more preferably from about 10 to about 150 microns. The particle size may vary depending upon the cross-sectional thickness of the structure to be fabricated. For example, in cross-sectional areas of thin widths, the particles may be of a small particle size such as from about 0.1 to about 40 microns, whereas in thicker cross-sections, larger particles may be included such as in the range of from about 40 to about 50 microns. EP Patent No. 523019, U.S. Pat. Nos. 4,689,197, 4,828,495, 4,980,124, 3,502,466, and 4,369,068 and copending, commonly assigned U.S. application Ser. No. 60/201,607 are directed to methods of and materials for making dental restorations using metal powders and are hereby incorporated by reference herein.

The MMC material comprises a mixture of metal and ceramic material. Preferred MMC materials comprise a dispersion of ceramic or glass-ceramic or glassy constituent in a metal matrix. Such dispersion may further be created by infiltration of glassy materials into an inter-penetrating network (IPN) of metal/alloy. An IPN can be generated via a controlled sintering technique of metal powders. Increased fracture toughness, inherent in such MMCs, will have a blunting effect on the propagation of cracks on the internal surface of the restorations.

The metal in the MMC material may comprise any of the metals listed above, singly or in combination, as used for the metal layer and may be prepared and applied as used above, in powder form and preferably mixed with a vehicle such as a binder as described above. The ceramic material may be in the form of powder, whiskers, fibers and the like in the size range of from about 0.01 to about 200 microns and preferably in the size range from about 0.02 to about 100 microns. Ceramic materials include glass-ceramics, glasses, glazes, and all-ceramic materials. Examples of ceramic materials include, but are not limited to, alumina, zirconia, magnesia, mullite, silica, spinel, silicates, titania, lithium disilicate, leucite, and lithium phosphate. The ceramic material is preferably in powder form and is mixed with the metal powder and binder. As stated above, the MMC material is applied to the internal side of the ceramic in any known manner including, but not, limited to electrolytic or electroless deposition, sol/gel deposition followed by pyrolysis, fusing (sintering), pressing, sputtering, chemical vapor deposition, ion bombardment, and vacuum deposition. Alternatively, the MMC layer may be applied in two steps whereby the metal matrix material is applied to the internal side of the ceramic by any known manner as stated above.

Thereafter, the ceramic material is applied to the metal matrix layer in any known manner as stated above. The ceramic material will fill the interstices or pores formed by the metal matrix to provide a dense composite network.

After the impervious layer has been applied to the core, the exterior surface of the core can be finished with various veneers such as opaque layers, incisal layers, shade layers, body porcelains, and the like to provide the required match to the neighboring teeth in the patient's mouth.

As an alternative embodiment, the metal or MMC layer may be formed prior to the ceramic core. In this embodiment, the die need not be oversized to compensate for the application of the impervious layer, since this is being formed first. The MMC material is applied to the die in any known fashion. Preferably, the MMC material is in the form of a sheet and is pressed onto a die, or is in powder formed and is applied to and pressed onto a die. The thickness of the MMC layer is the same as that described in the process above when the MMC material is applied to the ceramic core. The MMC core may also be formed in two steps as described in the process above.

A ceramic, glass, or glass-ceramic can then be fused or pressed to this metal or MMC layer by following their firing schedule. The glass-ceramic material preferably should have a fusion temperature range of about 100° C. below the melting temperature range of the MMC material.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of manufacturing dental restorations comprising;

fabricating a ceramic infrastructure; and subsequently disposing a layer on the internal side of the ceramic infrastructure, whereby the layer is comprises a metal-matrix ceramic composite, wherein the metal-matrix ceramic composite material comprises a dispersion of a ceramic, glass-ceramic or glass in a metal matrix, and whereby the layer is deposited in the form of a mixture of the metal in the metal matrix and the ceramic, glass-ceramic or glass.

2. The method of claim 1 wherein the layer is disposed by electrolytic deposition.

3. The method of claim 1 wherein the layer is disposed by applying and sintering the layer onto the internal side of the ceramic infrastructure.

4. The method of claim 1 wherein the ceramic infrastructure comprises one or more of glass-ceramic, alumina, zirconia, mullite, spinel, porcelain, titania, lithium disilicate, leucite, amorphous glass, and lithium phosphate.

5. The method of claim 1 wherein the metal in the metal matrix is selected from gold, silver, platinum group metals, titanium, tin, indium, gallium, antimony, and mixtures thereof.

6. The method of claim 1 wherein the metal in the metal-matrix is selected from gold, silver, platinum group metals, titanium, tin, indium, gallium, antimony, and mixtures thereof.

7. The method of claim 1 wherein the layer has a thickness below about 200 microns.

* * * * *

UNITED STATES PATENT AND TRADEMARK OFFICE
CERTIFICATE OF CORRECTION

PATENT NO. : 6,627,248 B1
DATED : September 30, 2003
INVENTOR(S) : Arun Prasad

It is certified that error appears in the above-identified patent and that said Letters Patent is hereby corrected as shown below:

Column 6,
Line 4, delete "formed" and replace with -- form --
Line 35, delete the word "is"

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,627,248 B1 Page 1 of 1
DATED : December 10, 2003
INVENTOR(S) : Arun Prasad It is certified that error appears in the above-identified patent and that said Letters Patent is hereby corrected as shown below:

Column 6,
Line 4, delete "formed" and replace with -- form --
Line 35, delete the word "is"

Signed and Sealed this

Tenth Day of February, 2004

JON W. DUDAS
*Acting Director of the United States Patent and Trademark Office*